US009908912B2

(12) United States Patent
Bovill et al.

(10) Patent No.: US 9,908,912 B2
(45) Date of Patent: Mar. 6, 2018

(54) TRICLOSAN DERIVATIVES AND USES THEREOF

(71) Applicant: Oxoid Limited, Hampshire (GB)

(72) Inventors: Richard Bovill, Hampshire (GB); Gemma Howse, Reading (GB)

(73) Assignee: Oxoid Limited, Hampshire (GB)

( * ) Notice: Subject to any disclaimer, the term of this patent is extended or adjusted under 35 U.S.C. 154(b) by 359 days.

(21) Appl. No.: 14/090,402

(22) Filed: Nov. 26, 2013

(65) Prior Publication Data

US 2014/0178923 A1    Jun. 26, 2014

(30) Foreign Application Priority Data

Dec. 21, 2012    (GB) .................................. 1223309.4

(51) Int. Cl.
*C07H 15/20* (2006.01)
*C12Q 1/04* (2006.01)
*C07H 15/203* (2006.01)

(52) U.S. Cl.
CPC ........... *C07H 15/20* (2013.01); *C07H 15/203* (2013.01); *C12Q 1/045* (2013.01); *G01N 2333/205* (2013.01); *G01N 2333/255* (2013.01)

(58) Field of Classification Search
CPC ...... C07H 15/20; C07H 15/203; C12Q 1/045; G01N 2333/255; G01N 2333/205
USPC ........................................... 435/34; 536/16.8
See application file for complete search history.

(56) References Cited

U.S. PATENT DOCUMENTS 5,447,849 A    9/1995 Toora

FOREIGN PATENT DOCUMENTS

| EP | 2723452 | 4/2014 |
|---|---|---|
| WO | 97/39140 A1 | 10/1997 |
| WO | 99/37800 | 7/1999 |
| WO | WO 2012/177986 | * 12/2012 |

OTHER PUBLICATIONS

Howse (2011). "The synthesis and determination of the antibacterial properties of targeted antibacterial agents" Ph.D. Dissertation (Abstract), Proquest ID: 1414910426.*

Sioufi et al. (1977). GLC Determination of Free and Conjugated Triclosan in Human Plasma and Urine. Journal of Pharmaceutical Sciences, v66(8), p. 1166-1168.*
Great Britain Search Report GB1223309.4, Jul. 30, 2013 (5 pages).
Laukkanen et al. Evaluation of isolation methods for pathogenic *Yersinia enterocolitica* from pig intestinal content. Journal of Applied Microbiology, 108 (2010) 956-964.
Van Damme et al. Effect of Sampling and Short Isolation Methodologies on the Recovery of Human Pathogenic *Yersinia enterocolitica* from Pig Tonsils. Foodborne Pathogens and Disease, 9 (2012) 600-606.
Saunders et al. Ecological effects of triclosan and triclosan monophosphate on defined mixed cultures of oral species grown in continuous culture. Journal of Antimicrobial Chemotherapy 45 (2000) 447-452.
Howse. The synthesis and determination of the antibacterial properties of targeted antibacterial agents. Doctoral Thesis, University of Reading 2011 (Abstract) (1 page).
UK IPO, Examination Report, UK App No. 1223309.4, dated Nov. 12, 2015, 5 pages.
*INPI, FR Written Opinion, FR App No. 1363175, dated Dec. 9, 2015, 9 pages. *English translation included, 4 pages.
Ballabene et al., "Evaluation of antimicrobial drugs and atmospheres for the isolation of Campylobacter fetus subspp. From the bovine genital tract," Revista Argentina de microbiologia, vol. 24, p. 113-125, 1992.
Haraszthy et al., "Media- and method-dependent variations in minimal inhibitory concentrations of antiplaque agents on oral bacteria," Letters in Applied Microbiology, vol. 43, p. 256-261, 2006.
Hundt et al., "Transformation of Triclosan by Trametes versicolor and Pycnoporus cinnabarinus," Applied and Environmental Microbiology, vol. 66, No. 9, p. 4157-4160, 2000.
Macherius et al., "Metabolization of the Bacteriostatic Agent Triclosan in Edible Plants and its Consequences for Plant Uptake Assessment," Environmental Science & Technology, vol. 46, p. 10797-10804, 2012.
Randall et al., "Effect of triclosan or a phenolic farm disinfectant on the selection antibiotic-resistant *Salmonella enterica*," Journal of Antimicrobial Chemotherapy, vol. 54, p. 621-627, 2004.

* cited by examiner

*Primary Examiner* — Sean C. Barron
(74) *Attorney, Agent, or Firm* — Baker & Hostetler LLP

(57) ABSTRACT

A selective agent comprising a triclosan derivative for use in selective inhibition of non-target cells in a mixed population of target and non-target cells. Preferably the triclosan derivative is a glycoside derivative, more preferably a pyranoside derivative. Suitably a selective medium comprising said selective agent and methods of culturing cells using the selective agent are provided.

7 Claims, 1 Drawing Sheet

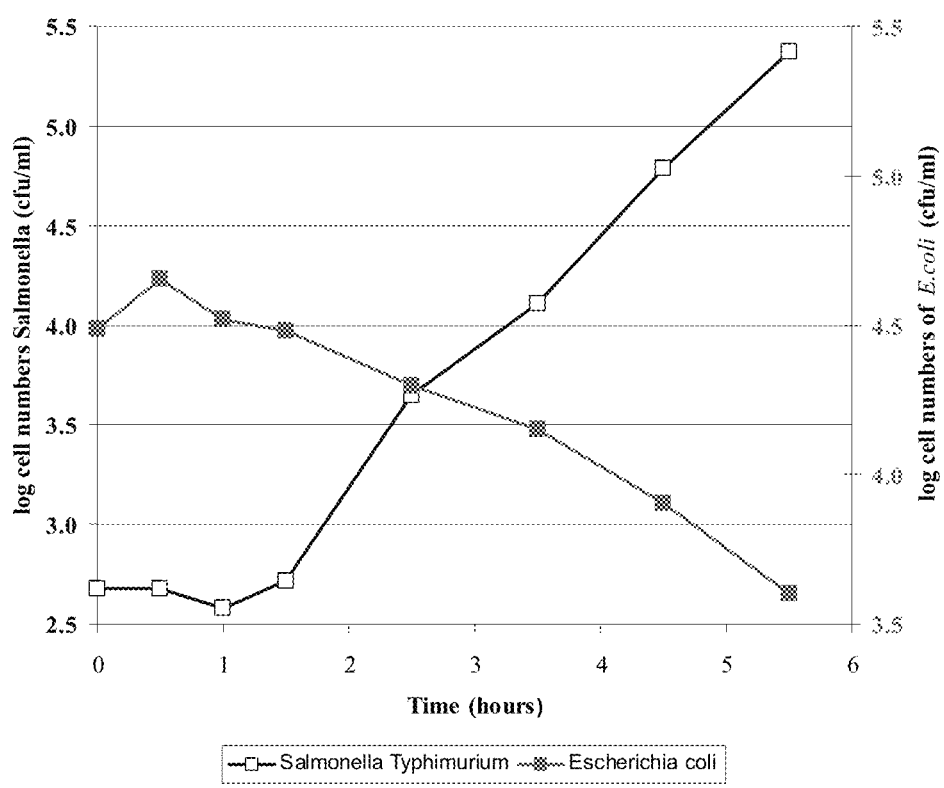

TRICLOSAN DERIVATIVES AND USES THEREOF

RELATED APPLICATIONS

This application claims priority to GB1223309.4 filed Dec. 21, 2012 which is expressly incorporated by reference herein in its entirety.

The present invention relates to triclosan derivatives and uses thereof, in particular selective agents comprising triclosan derivatives and selective media containing triclosan derivatives. The invention also concerns methods for selectively inhibiting the growth of certain cells in a mixed population using a selective agent comprising a triclosan derivative and kits for performing such methods.

BACKGROUND

The broad spectrum antimicrobial agent, 5-chloro-2-(2,4-dichlorophenoxy)phenol (also referred to as "triclosan" or "Irgasan®", which is Ciba Specialty Chemical's brand name for triclosan), has been commonly used since the early 1970's for personal hygiene products, including soap, toothpaste, deodorant, and for household and industrial cleaning products. Although at high concentrations triclosan is a biocide, at lower levels it functions as a bacteriostatic agent.

Despite the long history of antimicrobial use, triclosan alone has not been routinely used as a selective agent in differentiation media for preferential growth of particular bacterial species. U.S. Pat. No. 5,447,849 to Toora teaches the use of a combination of cefsulodin and triclosan for selective growth of *Yersinia enterocolitica*. U.S. Pat. No. 5,741,663 to Russell teaches the use of triclosan in combination with carbenicillin and nitrofurantoin for selective growth of *Pseudomonas fluorescens*. US Patent Application Publication 2010/0278847 to Good et al. teaches the addition of triclosan in the range of 100 nM to 10 µM to culture medium (which was also supplemented with ampicillin) for distinguishing genetically modified (transformed) *E. coli* showing vector-mediated expression of the gene for enoyl-ACP reductase (fab1). There is no disclosure in Good et al. relating to culture of naturally-occurring bacteria and/or fungi of the type typically found in environmental, industrial or medical samples.

SUMMARY OF THE INVENTION

According to a first aspect of the invention there is provided a selective agent comprising a triclosan derivative for use in selective inhibition of non-target cells in a mixed population of target and non-target cells.

The mixed populations are of the type found in environmental, industrial and/or clinical samples. The disclosed triclosan derivatives may be used without other antibiotics, inhibitory dyes, biocides or bacteriostatic agents. The conditions within which the microorganisms were existing at the time of collection as well as the conditions of transport of environmental, industrial and/or medical samples is generally stressful and potentially damaging. As a consequence, the target microorganisms within a sample may have weakened resistance to antibiotics and other inhibitory agents and often require an extended lag phase before resuming normal growth. The standard practice in many laboratories is to subject samples to pre-enrichment culture in a nutrient growth medium without antibiotics for a period of time sufficient to facilitate recovery of the target microorganisms, for example, approximately 16 hours. However, target cells are often present in lower numbers than non-target microorganisms and pre-enrichment culture can exacerbate this imbalance leading to overgrowth of non-target microorganisms and masking of target microorganisms.

Because the triclosan derivatives of the present invention and compositions containing such triclosan derivatives permit culture without antibiotics or other biocides, the need for pre-enrichment culture is eliminated for most samples, saving time and decreasing the risks associated with additional handling of samples to perform pre-enrichment recovery culture.

The invention further provides use of a triclosan derivative as a selective agent for selective inhibition of non-target cells in a mixed population of target and non-target cells.

The term "derivative" as used herein in relation to triclosan generally refers to a chemical substance derived from triclosan either directly or by modification or partial substitution.

The cells may be eukaryotic cells (e. g. mammalian cells, fungal cells or yeast cells) but more typically will be bacterial cells. In particular, the target and non-target cells will normally both comprise bacteria.

The term "inhibition" as used herein generally refers to inhibition of the growth of cells by decreasing, slowing or stopping growth of cells. As used herein, "growth" means increase in size or proliferation or both. Thus, a compound of this invention can inhibit cells by killing, inhibiting them from becoming larger, and/or can prevent cells from dividing and replicating and increasing in number. Overall, such inhibition prevents any net increase in viable cell numbers.

In preferred embodiments the selective agent is a composition for inclusion in a bacterial growth medium.

Preferably the triclosan derivative is a glycoside derivative of triclosan. In other words, the selective agent is a glycoside wherein the aglycone is triclosan. The sugar moiety is bonded to the triclosan moiety via an O-linkage. The triclosan is bonded to the anomeric carbon of a carbohydrate moiety.

Preferably the glycoside derivative of triclosan is a pyranoside derivative (i.e. a glycopyranoside of triclosan). In other words, the glycone moiety (i.e. the sugar moiety) of the glycoside includes a pyranose ring.

In preferred embodiments the triclosan glycoside derivative is selected from:
triclosan-α-D-arabinopyranoside,
triclosan-β-D-arabinopyranoside,
triclosan-α-D-galactopyranoside,
triclosan-β-D-galactopyranoside,
triclosan-α-D-glucopyranoside,
triclosan-β-D-glucopyranoside, and
triclosan-α-D-mannopyranoside.

In preferred embodiments, the selective agent has the general formula (I):

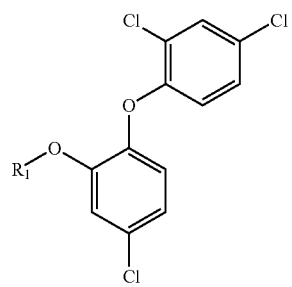

wherein $R_1$ is a glycone (i.e. $R_1$ is a sugar moiety). Preferably the $R_1$ group includes a pyranose ring.

In preferred embodiments a selective agent can be used, wherein the selective agent exerts a toxic effect on non-target cells when contacted with non-target cells, whereas the selective agent does not exert a toxic effect on target cells when contacted with target cells. The selective agent of the present invention may be used in any manner of situations where it is desired to cause inhibition of part of a mixed population of cells.

The selective agent suitably inhibits growth of non-target cells when contacted with non-target cells but is essentially non-inhibitory to target cells, whether stressed or unstressed, when contacted with target cells. When bacterial cells are placed in a suitable growth medium there is a 'lag phase' during which the net number of viable bacterial cells does not increase, or increases only slowly. After the lag phase, the culture enters an exponential growth phase in which the mean "generation time" (that is, the mean time taken for a number of cells to proceed from formation to fission) is at its shortest. As an illustration of what is considered 'essentially non-inhibitory', a selective agent will normally be considered essentially non-inhibitory to target cells at a particular concentration if it causes an increase in the lag phase of less than 25%, preferably less than 20% and more preferably less than 15% and if it causes an increase in the mean generation time, during the exponential growth phase, of less than 20%, preferably less than 10%, and more preferably less than 5%.

In a particular preferred embodiment, the selective agent is used in situations wherein the target cells are *Salmonella* spp. and the non-target cells are *E. coli* and/or other coliform bacteria. The selective agent allows *Salmonella* strains to grow, whilst inhibiting (i.e. preventing any net increase in viable cell numbers) competitor coliform organisms. The selective agent is substantially non-inhibitory to *Salmonella* strains, even those in a stressed state. Accordingly it is possible to reduce the overall culture time required for *Salmonella* strains (if present in the original sample) to attain the cell density required to give a positive result in any assay for the presence (e.g. ELISA, PCR etc), since their growth is not inhibited.

In an alternative embodiment the selective agent is used in situations wherein the target cells are *Campylobacter* spp. In other words, the selective agent is selective for *Campylobacter* spp.

Also provided is a medium for selective inhibition of non-target cells in a mixed population of target and non-target cells, the medium comprising a selective agent as defined above. The selective medium is typically a culture medium which provides inhibition of non-target cells in a mixed population of non-target and target cells. The medium may be liquid or solid and may comprise any of the components which may conventionally and suitably be included in media, such as a nutrient base, peptones, yeast extract, agar (or other solidifying agent), salts, buffers, indicator dyes and the like. Preferably the selective agent is provided in an effective amount to inhibit non-target cells.

The medium may include a suitable inducer. Use of a suitable inducer increases the inhibitory activity of the selective agent. Suitable inducers include methyl glycoside, isopropyl-β-D-thiogalactopyranoside, p-nitrophenyl-α-L-arabinopyranoside or p-nitrophenyl-β-D-xylopyranoside.

The selective agent is suitably provided in the medium at a suitable concentration which allows target cells to grow, whilst inhibiting non-target cells.

Suitably the invention also provides a medium, as defined above, in contact with a mixed population of target and non-target cells.

In a particularly preferred embodiment a culture medium is provided for differentiation of *Salmonella*, the culture medium comprising a selective agent as defined above. This provides a medium for differentiation of *Salmonella*, for example from coliform bacteria such as *E. coli*. The target cells are *Salmonella* spp and the non-target cells are coliforms, preferably *E. coli*. In this embodiment the selective agent is preferably triclosan β-D-galactopyranoside.

In alternative embodiments a culture medium for enumeration of *Campylobacter* spp is provided, the culture medium comprising a selective agent as defined above. This provides a culture medium for growth and enumeration of *Campylobacter* colonies. The applicant has found that the culture medium of the invention reduces or prevents false positives from the presence of multi-drug resistant Gram negative species. In this embodiment the selective agent is preferably triclosan β-D-galactopyranoside or triclosan α-D-arabinopyranoside. The invention also provides use of a selective agent or medium as defined above for the growth and enumeration of *Campylobacter*.

The invention further provides use of a triclosan derivative having any of the preferred features as hereinbefore mentioned as a selective agent or in a selective medium for selective inhibition of non-target cells in a mixed population of target and non-target cells.

In a further aspect, the invention provides a method of culturing bacteria, fungal or yeast cells in a sample suspected to contain a mixed population of target and non-target cells, the method comprising the steps of contacting the sample cells with a selective agent as defined above, wherein the selective agent is inhibitory to non-target cells but is essentially non-inhibitory to target cells, and culturing the cells in conditions which allow for growth of target cells. The method may utilise a medium as defined above.

The method may be performed without contacting the sample with a pre-enrichment medium that lacks the selective agent.

Prior to the culturing step, the number of non-target cells in the mixed population may be greater than the number of target cells in the mixed population.

It will be understood that performance of methods according to the invention may allow conclusions to be made regarding the identity of organisms which are able to grow successfully in the selective growth conditions. Thus, in some embodiments, the invention may comprise the further step of identifying target cell organisms which are able to grow in a culture comprising the selective agent. Alternatively, or additionally, the method may comprise the step of isolating colonies of the target cell organisms which are able to grow in a culture comprising the selective agent. Such methods of identification and/or isolation are routine for those skilled in the art.

According to the present invention there is further provided a kit for use with a method as defined above, comprising a medium containing a selective agent as defined above or components for preparing the same. The kit may further comprise instructions for performing the method according to the invention.

According to the present invention there is also provided a composition comprising a glycoside derivative of triclosan. In preferred embodiments the glycoside derivative of triclosan is a pyranoside derivative. In particularly preferred embodiments the pyranoside derivative of triclosan is selected from:
triclosan-α-D-arabinopyranoside,
triclosan-β-D-arabinopyranoside,
triclosan-α-D-galactopyranoside,
triclosan-β-D-galactopyranoside,
triclosan-α-D-glucopyranoside,
triclosan-β-D-glucopyranoside, and
triclosan-α-D-mannopyranoside.

The terms arabinoside, galactoside, glucoside and mannoside are used herein as shorthand to refer to the relevant glycone moiety.

In preferred embodiments, the selective agent has the general formula (I):

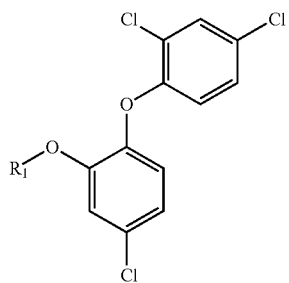

wherein $R_1$ is a glycone (i.e. $R_1$ is a sugar moiety). Preferably the $R_1$ group includes a pyranose ring.

DESCRIPTION OF FIGURES

Preferred embodiments of the present invention will now be more particularly described by way of example only with reference to the accompanying drawings, wherein:

FIG. 1 shows a graph of the growth of a mixed culture of *E. coli* 607 and *Salmonella* typhimurium 722 in Nutrient Broth No. 2 containing triclosan-β-D-galactoside (2 (μg/ml) at 37° C.

DETAILED DESCRIPTION OF THE INVENTION

Triclosan Derivatives

Triclosan derivatives of the present invention comprise glycoside derivatives of the biocide wherein the phenolic group of triclosan is coupled to the anomeric sugar hydroxyl. Exemplary methods of making triclosan glycosides are provided in Examples 1-4. Examples of glycosides include, without limitation, α-D-arabinopyranoside, β-D-arabinopyranoside, α-D-galactopyranoside, β-D-galactopyranoside, α-D-glucopyranoside, β-D-glucopyranoside, and α-D-mannopyranoside.

As shown in Table 1, virtually all microorganisms showed a greater minimum inhibitory concentration ("MIC") for triclosan glycoside derivatives than for free triclosan. Triclosan (Irgasan®, Ciba Specialty Chemicals) or Triclosan-β-D-galactoside was added in varying concentrations to Nutrient Broth No. 2 (Oxoid CM0067, Thermofisher Scientific). Bacteria species as indicated in Table 1 were incubated for approximately 24 hours at 37° C. Minimum inhibitory concentrations (MIC) of each selective agent were determined as the lowest concentration (μg/ml) required to completely inhibit growth (as determined by measuring absorption at 600 nm using a Bioscreen instrument; Oy Growth Curves Ab Ltd) during a 24-hour incubation time.

All of the organisms that were tested were inhibited by triclosan but several were totally resistant to its glycosides (Table 1).

TABLE 1

MICs of Triclosan-glycosides in Nutrient Broth No. 2

| | | | α-D-Glucoside | | α-D-Galactoside | | α-D-Arabinoside | | α-D-Mannoside | |
|---|---|---|---|---|---|---|---|---|---|---|
| Strains | No. of Strains | Underivatised Triclosan | without inducer | with inducer | without inducer | with inducer | without inducer | with inducer | without inducer | with inducer |
| Gram-negative organisms | | | | | | | | | | |
| *Aeromonas hydrophila* OCC 778 | 1 | 8 | 256 | 256 | >256 | >256 | 128 | 256 | >256 | >256 |
| *Citrobacter freundii* OCC 851 | 1 | 0.5 | 4 | 4 | 64 | 128 | 8 | 8 | 64 | 64 |
| *Crono. sakazakii* ATCC 29544 | 1 | 0.5 | 8 | 4 | 128 | 64 | 8 | 16 | 128 | 32 |
| *Enterobacter aerogenes* ATCC 13048 | 1 | 0.5 | 8 | 4 | 128 | 64 | 8 | 16 | 32 | 32 |
| *Ent. cloacae* ATCC 13047 | 1 | 0.5 | 1 | 1 | 32 | 16 | 0.5 | 0.5 | 8 | 8 |
| *Escherichia coli* | 8 | 0.1 to 0.5 | 2 to 8 | 1 to 4 | 16 to 64 | 8 to 64 | 0.5 to 4 | 0.5 to 8 | 4 to 64 | 4 to 32 |
| *E. hermanii* ATCC 33650 | 1 | 0.5 | 1 | 1 | 32 | 32 | 1 | 2 | 16 | 8 |
| *Hafnia alvei* ATCC 13337 | 1 | 0.1 | 1 | 1 | 16 | 8 | 0.5 | 0.5 | 4 | 4 |
| *Kleb. aerogenes* NCTC 88167 | 1 | 0.5 | 2 | 4 | 32 | 64 | 4 | 4 | 32 | 32 |
| *Kleb. pneumoniae* ATCC 10031 | 1 | 0.1 | 1 | 1 | 1 | 1 | 0.5 | 0.5 | 4 | 2 |
| *Proteus mirabilis* ATCC 12453 | 1 | 0.5 | 2 | 2 | 32 | 32 | 4 | 2 | 16 | 8 |

TABLE 1-continued

MICs of Triclosan-glycosides in Nutrient Broth No. 2

| Strains | | | | | | | | | |
|---|---|---|---|---|---|---|---|---|---|
| Proteus vulgaris OCC 195 | 1 | 0.5 | 4 | 4 | 64 | 64 | 16 | 8 | 32 | 32 |
| Ps. Aeruginosa ATCC 27853 | 1 | 32 | >256 | >256 | >256 | >256 | >256 | >256 | >256 | >256 |
| Salmonella | 11 | 0.5 to 1 | 2 to 8 | 1 to 4 | 32 to 64 | 32 to 128 | 2 to 8 | 2 to 8 | 16 to 64 | 8 to 32 |
| Serratia marcescens OCC 217 | 1 | 64 | >256 | >256 | >256 | >256 | >256 | >256 | >256 | >256 |

| | | | β-D-Glucoside | | β-D-Galactoside | | β-D-Arabinoside | |
|---|---|---|---|---|---|---|---|---|
| Strains | No. of Strains | Underivatised Triclosan | without inducer | with inducer | without inducer | with inducer | without inducer | with inducer |
| Gram-negative organisms | | | | | | | | |
| Aeromonas hydrophila OCC 778 | 1 | 8 | >256 | 256 | 256 | 256 | >256 | >256 |
| Citrobacter freundii OCC 851 | 1 | 0.5 | 64 | 8 | 8 | 8 | 64 | 64 |
| Crono. sakazakii ATCC 29544 | 1 | 0.5 | 64 | 8 | 8 | 8 | 128 | 64 |
| Enterobacter aerogenes ATCC 13048 | 1 | 0.5 | 64 | 16 | 8 | 16 | 128 | 64 |
| Ent. cloacae ATCC 13047 | 1 | 0.5 | 16 | 1 | 0.5 | 0.1 | 16 | 16 |
| Escherichia coli | 8 | 0.1 to 0.5 | 8 to 64 | 1 to 8 | 0.5 to 32 | 0.5 to 4 | 8 to 32 | 4 to 32 |
| E. hermanii ATCC 33650 | 1 | 0.5 | 16 | 2 | 2 | 2 | 32 | 16 |
| Hafnia alvei ATCC 13337 | 1 | 0.1 | 4 | 0.5 | 0.5 | 0.5 | 4 | 4 |
| Kleb. aerogenes NCTC 88167 | 1 | 0.5 | 32 | 4 | 4 | 4 | 32 | 32 |
| Kleb. pneumoniae ATCC 10031 | 1 | 0.1 | 0.5 | 0.5 | 0.5 | 0.1 | 4 | 8 |
| Proteus mirabilis ATCC 12453 | 1 | 0.5 | 16 | 2 | 4 | 2 | 32 | 16 |
| Proteus vulgaris OCC 195 | 1 | 0.5 | 64 | 8 | 8 | 4 | 128 | 64 |
| Ps. Aeruginosa ATCC 27853 | 1 | 32 | >256 | >256 | >256 | >256 | >256 | >256 |
| Salmonella | 11 | 0.5 to 1 | 16 to 32 | 2 to 8 | 2 to 16 | 2 to 8 | 32 to 64 | 32 to 64 |
| Serratia marcescens OCC 217 | 1 | 64 | >256 | >256 | >256 | >256 | >256 | >256 |

| | | | α-D-Glucoside | | α-D-Galactoside | | α-D-Arabinoside | | α-D-Mannoside | |
|---|---|---|---|---|---|---|---|---|---|---|
| Strains | No. of Strains | Underivatized Triclosan | without inducer | with inducer | without inducer | with inducer | without inducer | with inducer | without inducer | with inducer |
| Gram-positive organisms | | | | | | | | | | |
| Bacillus cereus ATCC 14579 | 1 | 2 | 128 | 128 | >256 | >256 | 128 | 128 | 256 | 256 |
| Bacillus subtilis NCTC 10073 | 1 | 1 | 32 | 32 | 256 | >256 | 32 | 32 | 128 | 256 |
| Enterococcus faecalis ATCC 29212 | 1 | 8 | 128 | 128 | >256 | >256 | 128 | 128 | 256 | 256 |
| Enterococcus faecium ATCC 19434 | 1 | 4 | 256 | 256 | >256 | >256 | 256 | 256 | 256 | 256 |
| Staph. aureus | 8 | 0.01 | 1 | 1 | 8 to 16 | 8 to 16 | 0.5 | 0.5 | 2 to 8 | 2 to 8 |
| Staph. epidermidis | 3 | 0.01 | 1 | 1 | 8 to 32 | 4 to 256 | 0.5 | 0.5 | 4 to 8 | 4 to 8 |

TABLE 1-continued

MICs of Triclosan-glycosides in Nutrient Broth No. 2

| Strains | | | | | | | | | | |
|---|---|---|---|---|---|---|---|---|---|---|
| Staph. haemolyticus OCC 2223 | 1 | 0.01 | 1 | 1 | 16 | 32 | 0.5 | 0.5 | 8 | 8 |
| Staph. saprophyticus ATCC 15305 | 1 | 0.01 | 4 | 4 | 64 | 64 | 8 | 8 | 32 | 32 |
| Strep. agalactiae OCC 182 | 1 | 4 | 128 | 128 | >256 | >256 | 128 | 128 | 128 | 128 |
| Strep. pneumoniae ATCC 6305 | 1 | 1 | 32 | 16 | 128 | 256 | 64 | 32 | 64 | 128 |
| Strep. pyogenes ATCC 19615 | 1 | 1 | 32 | 16 | 256 | 256 | 16 | 8 | 32 | 32 |
| Strep. viridans OCC 234 | 1 | 4 | 128 | 64 | >256 | >256 | 128 | 128 | 128 | 128 |

| Strains | No. of Strains | Underivatized Triclosan | β-D-Glucoside | | β-D-Galactoside | | β-D-Arabinoside | |
|---|---|---|---|---|---|---|---|---|
| | | | without inducer | with inducer | without inducer | with inducer | without inducer | with inducer |
| Gram-positive organisms | | | | | | | | |
| Bacillus cereus ATCC 14579 | 1 | 2 | 256 | 128 | 256 | 256 | 128 | 128 |
| Bacillus subtilis NCTC 10073 | 1 | 1 | 256 | 32 | 32 | 32 | 128 | 128 |
| Enterococcus faecalis ATCC 29212 | 1 | 8 | 16 | 128 | 128 | 128 | 256 | 256 |
| Enterococcus faecium ATCC 19434 | 1 | 4 | >256 | 256 | >256 | >256 | 256 | 256 |
| Staph. aureus | 8 | 0.01 | 4 to 8 | 0.5 to 2 | 0.5 | 0.5 | 4 to 8 | 4 to 8 |
| Staph. epidermidis | 3 | 0.01 | 8 to 16 | 0.5 to 1 | 0.5 | 0.5 | 8 to 16 | 4 to 64 |
| Staph. haemolyticus OCC 2223 | 1 | 0.01 | 16 | 0.5 | 0.5 | 0.5 | 128 | 16 |
| Staph. saprophyticus ATCC 15305 | 1 | 0.01 | 64 | 8 | 8 | 8 | 64 | 64 |
| Strep. agalactiae OCC | 1 | 4 | 256 | 128 | 256 | 256 | 128 | 128 |
| Strep. pneumoniae ATCC 6305 | 1 | 1 | 128 | 64 | 128 | 128 | 64 | 64 |
| Strep. pyogenes | 1 | 1 | 32 | 16 | 128 | 128 | 32 | 32 |
| Strep. viridans OCC 234 | 1 | 4 | 256 | 128 | 256 | >256 | 128 | 128 |

Example 1

Acetylation of Sugars

A suspension of 30.0 mmoles of the sugar in 10 ml (129 mmoles) of anhydrous pyridine under an argon atmosphere was cooled in ice with stirring. Acetic anhydride (10 ml, 0.09 mol) was then added drop-wise and the reaction stirred at room temperature for 18 hours. The solution was then concentrated in vacuo, azeotroping with toluene. The resulting residue was dissolved in dichloromethane (50 ml), and washed with 1M HCl (2×50 ml), saturated aqueous NaHCO$_3$ solution (2×50 ml) and brine (2×50 ml). The dichloromethane layer was then dried with magnesium sulphate, filtered and concentrated in vacuo to yield the product as a white powder.

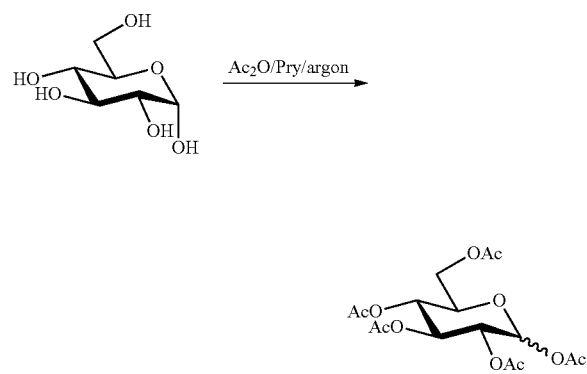

Example 2

Bromination

To 13.0 mmoles of the acetylated sugar from Example 1, cooled to 0° C., 36.7 mmoles of HBr in glacial acetic acid (45% w/v) was added drop-wise. The solution was stirred at 0° C. for 3 hours, then it was poured onto ice and extracted with CH$_2$Cl$_2$ (2×100 ml). The combined extracts were washed with saturated aqueous NaHCO$_3$ solution (2×100 ml), then dried with anhydrous magnesium sulphate, filtered and concentrated in vacuo to yield a clear orange syrup. The syrup was dissolved in ethyl acetate and crystallized as a white powder.

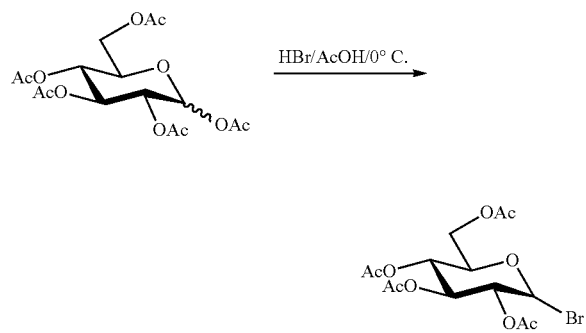

Example 3

Method 1 for Glycosidation

Use of the Koenigs-Knorr method ensured that only the trans anomeric form of the glycoside was formed.

Triclosan (4.04 g, 14.0 mmoles) was dissolved in 100 ml of water containing 14 ml of a 1M sodium hydroxide solution (14 mmoles) and 40 ml of acetone. To the stirred solution was then added 60 ml of a solution of acetobromogalactose (13.2 mmoles) in acetone in one go. The reaction mixture was stirred at room temperature for 18 hours then solvent was removed in vacuo. The crude product was purified by flash chromatography (silica gel eluted with a 3:2 mixture of hexane/ethyl acetate) to yield the product.

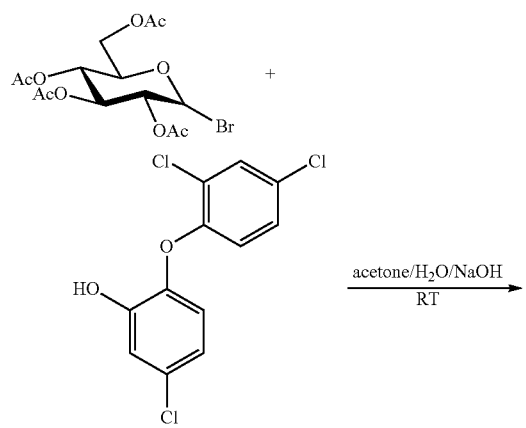

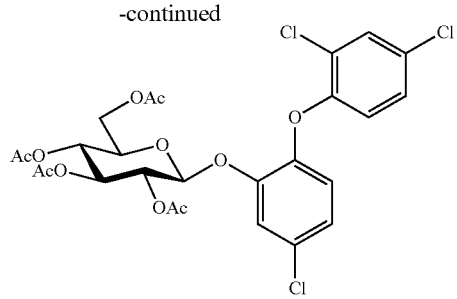

Example 4

Method 2 for Glycosidation

As an alternative method, both α- and β-anomers are formed and may be separated using flash chromatography.

Under argon, the acetylated sugar (17.0 mmoles) was dissolved in 100 ml of anhydrous dichloromethane and triclosan (18.0 mmoles) was then added. To the stirred solution at 0° C. was then added boron trifluoride etherate (51.0 mmoles). The reaction was then allowed to warm to room temperature and stirred for 18 hours. Water (20 ml) was added to quench the reaction, which was then stirred for a further 15 minutes. Then 50 ml of dichloromethane was added and the solution was washed with water (2×150 ml) and brine (2×150 ml) and dried with magnesium sulphate. After filtering, solvent was removed in vacuo and the crude product was purified by flash chromatography (silica gel eluted with a 3:2 mixture of hexane/ethyl acetate).

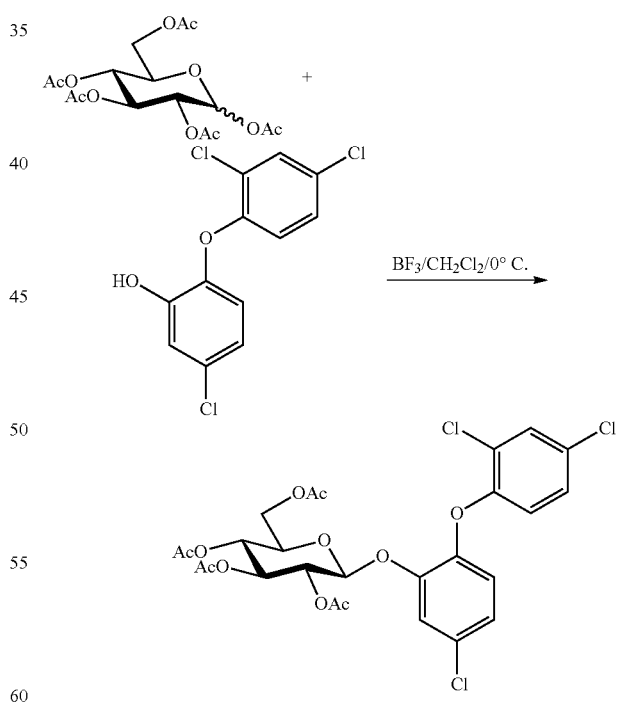

General Procedure: Deprotections

Under argon, the protected sugar (1 eq) was dissolved in anhydrous MeOH (1 ml per mmol). K$_2$CO$_3$ (0.1 eq) was then added. The reaction was then stirred until it was deemed to be complete as evidenced by TLC analysis. Amberlite IR-120 (plus) resin was then added and the reaction was stirred for a further 30 minutes. The resin was then filtered off and the filtrate concentrated in vacuo to yield the desired product.

Example 5

FIG. 1 shows the growth of a mixed culture of *E. coli* 607 and *Salmonella* typhimurium 722 in Nutrient Broth No. 2 containing triclosan-β-D-galactoside (2 (μg/ml) at 37° C. Samples were taken approximately every 30 minutes and plated onto Nutrient Agar. Although *E. coli* 607 showed a slight increase in number from $1.0 \times 10^4$ to $1.86 \times 10^4$ after 30 minutes, numbers then decreased to $3.98 \times 10^3$ cfu/ml after 7 hours. In contrast, *Salmonella* typhimurium 722, after a brief lag period of 1.5 hours, entered a normal logarithmic growth phase (doubling time=28.5 minutes) and after 7 hours had increased to $2.51 \times 10^5$ cfu/ml. Because in typical samples background microorganisms are present in much greater numbers than the target organism, for this experiment initial numbers of *E. coli in the mixed culture were* 1.5 log cfu/ml higher than *Salmonella* typhimurium.

Example 6

Multi-drug resistant Gram-negative microorganisms including *Acinetobacter baumanii* and species of Enterobacteriaceae are starting to appear in the food chain due to widespread agricultural antibiotic use. These microorganisms can appear as false positives on enumeration agar for *Campylobacter*.

*Campylobacter* species are unusual in their nutritional requirements in that they require only amino acids and TCA cycle intermediates for growth and do not utilize carbohydrates. The inventors have discovered that *Campylobacter* are resistant to glycoside derivatives of triclosan. Triclosan-β-D-galactoside and triclosan-α-arabinoside both have low MIC values for organisms of Enterobacteriaceae and were, therefore, chosen for examination. The triclosan compounds were added to Brilliance CampyCount agar (Oxoid) and organisms multi-point inoculated onto the surface of the plates. Plates were incubated for 24 hours at 37° C. in microaerobic conditions. Both compounds inhibited growth of all of the *A. baumanii* strains tested (Table 2). Triclosan-β-galactoside was particularly active in inhibiting two carbapenemase-producing strains of *Klebsiella pneumoniae* when used at 5 μg/ml while all *Campylobacter* strains were resistant to triclosan-α-arabinoside at concentrations as high as 50 μg/ml.

TABLE 2

MIC values for *Campylobacter* and interfering organisms (μg/ml)

| Organism | Triclosan-α-Arabinoside | Triclosan-β-galactoside |
|---|---|---|
| *Acinetobacter baumanii* GOXA23 | 40 | 40 |
| *Acinetobacter baumanii* Strain 99 | 40 | 30 |
| *Acinetobacter baumanii* OCC834 | 30 | 20 |
| *Acinetobacter baumanii* SE clone B | 40 | 40 |
| *Acinetobacter baumanii* OXA23 | 30 | 40 |
| *Acinetobacter baumanii* E36 OXa23 | 50 | 50 |
| *Campylobacter coli* OCC776 | >50 | >50 |
| *Campylobacter jejuni* OCC1596 | >50 | >50 |
| *Campylobacter jejuni* OCC1261 | >50 | >50 |
| *Campylobacter jejuni* OCC2340 | >50 | >50 |
| *Campylobacter lari* OCC1598 | >50 | >50 |
| *Campylobacter coli* OCC2774 | >50 | >50 |
| *Klebsiella pneumoniae* KPC2 | >50 | 5 |

TABLE 2-continued

MIC values for *Campylobacter* and interfering organisms (μg/ml)

| Organism | Triclosan-α-Arabinoside | Triclosan-β-galactoside |
|---|---|---|
| *Klebsiella pneumoniae* 7KPC3 | >50 | 5 |
| *Enterobacter cloacae* CTXm9 | 10 | 5 |

Example 7

Various glycoside derivatives of triclosan were added to 64 μg/ml of Nutrient Broth No. 2 to determine minimum inhibitory concentrations (MIC) of each selective agent and the results are shown in Table 1. The tests were repeated with the addition of inducers. Methyl glycoside was the main inducer used, but other suitable inducers include isopropyl-β-D-thiogalactopyranoside, p-nitrophenyl-α-L-arabinopyranoside and p-nitrophenyl-β-D-xylopyranoside. Concentration of inducer in all cases was 100 μg/ml.

From Table 1 it can be seen that the addition of triclosan-α-D-mannoside to Nutrient Broth at 64 μg/ml may allow the growth and recovery of *Cronobacter sakazakii*, an important pathogen found in particular in infant formula milk, but would inhibit the growth of many of the organisms that are often isolated with the organism. Thus, all strains of *Citrobacter freundii*, *Enterobacter cloacae*, *Escherichia coli*, *Escherichia hermanii*, *Hafnia alvei*, *Klebsiella*, *Proteus*, *Salmonella* and *Staphylococcus* were inhibited by this concentration. In addition Triclosan-β-D-arabinoside at 16 μg/ml would allow the selective recovery of *Salmonella* and triclosan-α-D-glucoside would allow the selective recovery of pathogenic strains of *Streptococcus*.

It was also observed that the addition of inducers substantially increased the inhibitory activity of the triclosan glycosides.

Example 8

Method for the Determination of Minimum Inhibitory Concentrations in Nutrient Agar The triclosan-glycosides were added to Nutrient Agar (Oxoid CM0003; Thermofisher Scientific) and organisms were transferred onto the plates surface using a multi-point inoculation device (Oxoid Cathra, Thermofisher Scientific). The latter is essentially a metal plate containing a number of needles. Each needle tip (usually 36 per plate) dips into an organism suspension (in phosphate buffered saline; PBS) and the needles are then moved over the agar plate and lowered onto its surface. In this way the growth of colonies of up to 36 different organisms can be observed on one plate.

Nutrient Agar No. 2 was prepared according to the manufacturers instructions, autoclaved and cooled to 50° C. Test compounds were then added as filter sterilised solutions (50:50 deionised water:ethanol), to give final concentrations from 256 μg/ml to 0 μg/ml in doubling dilutions. Inducers were also added at a final concentration of 0.1 mg/ml. The mixtures were swirled then four plates (25 ml molten agar) were poured for each concentration. Plates were dried in a laminar flow cabinet then inoculated with overnight cultures of organisms that had been decimally diluted twice in sterile saline solution (approximately $10^7$ cfu/ml) using a multi-point inoculator. Plates were then incubated at 37° C. for 24 hours. MICs were determined as the concentration at which no growth was observed.

The results are shown in Table 3. MICs obtained from the plates were similar to those obtained in broth indicating that the surface tension of the agar did not stress cells to any great extent. It also showed that free triclosan released from susceptible organisms did not inhibit more resistant organisms on the plates and the glycosides could, therefore be used for the recovery of mixed cultures.

TABLE 3

MICs of Triclosan-glycopyranosides (μg/ml) in Nutrient Agar containing 0.1 μg/ml of inducer

| Organisms | No. of Strains | α-D-arabinopyranoside | α-D-galactopyranoside | α-D-glucopyranoside | α-D-mannopyranoside | β-D-arabinopyranoside | β-D-galactopyranoside | β-D-glucopyranoside |
|---|---|---|---|---|---|---|---|---|
| Bacillus cereus | 1 | 128 | >256 | 64 | 128 | 256 | 256 | 256 |
| Bacillus subtilis | 1 | 128 | 128 | 16 | 256 | 256 | 64 | 256 |
| Ent. faecalis | 1 | 256 | >256 | 128 | 256 | 256 | >256 | >256 |
| Ent. faecium | 1 | 256 | >256 | 128 | 256 | 256 | >256 | >256 |
| S. aureus | 8 | 1 to 2 | 4 to 8 | 0.25 to 1 | 4 to 8 | 8 to 16 | 2 | 4 to 8 |
| S. epidermidis | 3 | 2 to 64 | 8 | 0.5 to 1 | 8 | 16 | 4 | 8 to 16 |
| S. haemolyticus | 1 | 2 | 8 | 1 | 8 | 16 | 4 | 16 |
| S. saprophyticus | 1 | 128 | 32 | 4 | 32 | 64 | 16 | 32 |
| Str. agalactiae | 1 | 128 | >256 | 128 | 128 | 128 | 256 | >256 |
| Str. pneumoniae | 1 | 64 | 256 | 32 | 64 | 64 | 64 | 128 |
| Str. pyogenes | 1 | 128 | >256 | 64 | 64 | 64 | 256 | 64 |
| Str. viridans | 1 | 128 | >256 | 64 | 128 | 128 | 256 | 256 |
| Aer. hydrophila | 1 | 128 | >256 | 128 | 256 | 256 | 256 | >256 |
| C. freundii | 1 | 16 | 64 | 4 | 64 | 64 | 8 | 64 |
| Cr. sakazakii | 1 | 16 | 32 | 4 | 64 | 256 | 64 | 32 |
| Ent. aerogenes | 1 | 16 | 64 | 4 | 64 | 64 | 16 | 32 |
| Ent. cloacae | 1 | 4 | 32 | 1 | 16 | 16 | 1 | 16 |
| E. coli | 8 | 2 to 8 | 8 to 32 | 0.5 to 4 | 8 to 64 | 8 to 32 | 1 to 4 | 16 to 32 |
| E. hermanii | 1 | 4 | 32 | 1 | 16 | 32 | 4 | 16 |
| Hafnia alvei | 1 | 2 | 4 | 0.5 | 4 | 8 | 2 | 8 |
| Kleb. aerogenes | 1 | 8 | 32 | 2 | 32 | 64 | 8 | 32 |
| Kleb. pneumoniae | 1 | 2 | 16 | 0.5 | 16 | 8 | 1 | 4 |
| Ps. aeruginosa | 1 | >256 | >256 | >256 | >256 | >256 | >256 | >256 |
| Salmonella | 11 | 4 to 16 | 8 to 64 | 1 to 4 | 16 to 32 | 32 to 64 | 4 to 16 | 16 to 128 |
| Ser. marcescens | 1 | >256 | >256 | >256 | >256 | >256 | >256 | >256 |

The invention claimed is:

1. A bacterial culture medium comprising nutrients supporting growth of the target bacteria cells and a selective agent comprising a glycoside derivative of triclosan, wherein the triclosan glycoside derivative is selected from the group consisting of:
   triclosan-α-D-arabinopyranoside,
   triclosan-β-D-arabinopyranoside,
   triclosan-α-D-galactopyranoside,
   triclosan-β-D-galactopyranoside,
   triclosan-α-D-glucopyranoside,
   and
   triclosan-α-D-mannopyranoside,
the bacterial culture medium selectively inhibiting non-target bacteria cells in a mixed population of target and non-target bacteria cells.

2. The medium according to claim 1, in contact with a mixed population of target and non-target cells.

3. A bacterial culture medium comprising nutrients supporting the growth of Salmonella spp and a selective agent comprising a glycoside derivative of triclosan, wherein the triclosan glycoside derivative is selected from the group consisting of:
   triclosan-α-D-arabinopyranoside,
   triclosan-β-D-arabinopyranoside,
   triclosan-α-D-galactopyranoside,
   triclosan-β-D-galactopyranoside,
   triclosan-α-D-glucopyranoside,
   and
   triclosan-α-D-mannopyranoside
the bacterial culture medium differentiating Salmonella spp.

4. A bacterial culture medium comprising nutrients supporting the growth of Campylobacter spp and a selective agent comprising a glycoside derivative of triclosan, wherein the triclosan glycoside derivative is selected from the group consisting of:
   triclosan-α-D-arabinopyranoside,
   triclosan-β-D-arabinopyranoside,
   triclosan-α-D-galactopyranoside,
   triclosan-β-D-galactopyranoside,
   triclosan-α-D-glucopyranoside,
   and
   triclosan-α-D-mannopyranoside
the bacterial culture medium enumerating Campylobacter spp.

5. A method of culturing bacteria, fungal or yeast cells in a sample suspected to contain a mixed population of target and non-target cells, the method comprising the steps of
   contacting the sample cells in the bacterial culture medium of claim 1 with the selective agent, wherein the selective agent is inhibitory to non-target cells but is essentially non-inhibitory to target cells,
   and culturing the cells in conditions which allow for growth of target cells.

6. The method according to claim 5, wherein the method is performed without contacting the sample with a pre-enrichment medium that lacks the selective agent.

7. The method according to claim 5 or 6, wherein prior to the culturing step, the number of non-target cells in the mixed population is greater than the number of target cells in the mixed population.

* * * * *